United States Patent
Schoeneck et al.

(10) Patent No.: US 8,499,669 B2
(45) Date of Patent: Aug. 6, 2013

(54) METHODS AND APPARATUS FOR SINGULATING MICRO-WELL TAPE

(75) Inventors: Richard Schoeneck, Alexandria, MN (US); Brent Urke, Alexandria, MN (US); Adnanul Haq, Alexandria, MN (US); Paul Wagner, Alexandria, MN (US); Bruce Peterson, Alexandria, MN (US)

(73) Assignee: Douglas Machine Inc., Alexandria, MN (US)

( * ) Notice: Subject to any disclaimer, the term of this patent is extended or adjusted under 35 U.S.C. 154(b) by 271 days.

(21) Appl. No.: 12/864,512

(22) PCT Filed: Jan. 22, 2009

(86) PCT No.: PCT/US2009/031690
§ 371 (c)(1),
(2), (4) Date: Jul. 26, 2010

(87) PCT Pub. No.: WO2009/094448
PCT Pub. Date: Jul. 30, 2009

(65) Prior Publication Data
US 2010/0307305 A1 Dec. 9, 2010

Related U.S. Application Data

(60) Provisional application No. 61/023,850, filed on Jan. 26, 2008.

(51) Int. Cl.
*H01L 21/673* (2006.01)

(52) U.S. Cl.
USPC ............................... 83/23; 83/409

(58) Field of Classification Search
USPC ............... 422/522; 53/329; 83/23, 401, 409, 83/418, 422
See application file for complete search history.

(56) References Cited

U.S. PATENT DOCUMENTS

| | | | |
|---|---|---|---|
| 6,408,595 B1 * | 6/2002 | Friedman | 53/329 |
| 6,878,345 B1 | 4/2005 | Astle | |
| 2004/0071599 A1 * | 4/2004 | Rusch et al. | 422/99 |
| 2010/0303689 A1 * | 12/2010 | Peterson et al. | 422/553 |

FOREIGN PATENT DOCUMENTS

WO    WO 02/02405 A1    1/2002

* cited by examiner

*Primary Examiner* — Stephen Choi
(74) *Attorney, Agent, or Firm* — Alan Kamrath; Kamrath IP Lawfirm, P.A.

(57) ABSTRACT

An apparatus (10) for singulating micro-well tape includes a tape drive (12) and a cutting assembly (14). The micro-well tape is advanced into and passes between upper and lower tape retainers (44, 45), with the upper tape retainer (44) including a groove (441) into which a raised ridge (451) of a multiplicity of ridges (450) of the bottom tape retainer (45) extends, with the rows of wells moving between adjacent ridges (450) in a movement direction. When a bar code on the micro-well tape is detected by a sensor 24, a knife blade (30) mounted on a slide block (32) is moved vertically to cut the micro-well tape. The new leading edge of the micro-well tape pushes the cut micro-well tape which is deflected by the raised ridge (451).

12 Claims, 5 Drawing Sheets

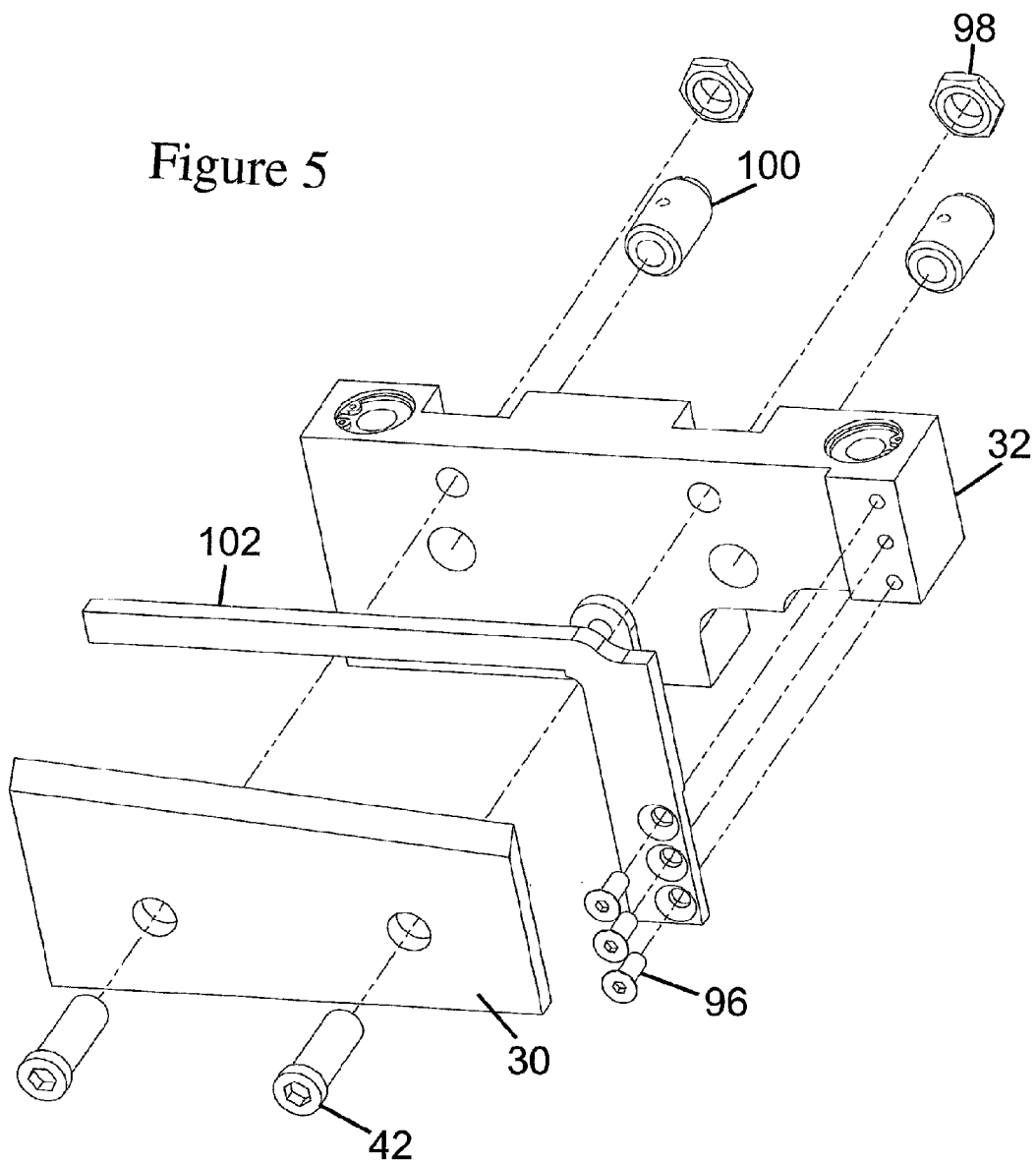

METHODS AND APPARATUS FOR SINGULATING MICRO-WELL TAPE

BACKGROUND

The present invention generally relates to methods and apparatus for singulating micro-well tape.

DNA samples have been traditionally processed in individual micro array trays with matrices of 96, 384 or 1536 wells. These trays are filled, processed and then inserted into various commercially available readers to record the results. Because of cost savings, this process is being moved from trays to micro-well tape. However, without adaptors, the micro-well tape cannot be run in readers being used in the industry.

Thus, a need exists to sever (singulate) matrices of tape to facilitate their processing such as but not limited to being inserted into adaptors so that the severed tape piece and adaptor can be utilized as an individual micro-array tray in the industry.

SUMMARY

The present invention solves this need and other problems in the field of severing micro-well tape to facilitate their further processing by providing, in most preferred aspects, a restricted space between upper and lower tape retainers such that a new leading edge of the micro-well tape pushes against the trailing edge of a cut micro-well tape deflected into a corrugated shape between the upper and lower tape retainers. In most preferred aspects, the cut micro-well tape is deflected by a raised ridge of a multiplicity of ridges between which the rows of the array of wells of the micro-well tape move in a movement direction. In most preferred aspects, the upper and lower tape retainers have tapered entries, and the upper tape retainer includes a groove into which the raised ridge extends.

In preferred aspects, the micro-well tape is advanced by a tractor drive including a backer plate including a multiplicity of ridges corresponding to the multiplicity of ridges on the bottom tape retainers. The tractor drive position is coordinated with a sensor detecting a bar code on the micro-well tape.

In further preferred aspects, the micro-well tape is cut by sliding a slide block on slide shafts and upon which a cutting knife blade is mounted from below the micro-well tape to a position where the cutting knife blade engages an anvil positioned above the micro-well tape.

The present invention will become clearer in light of the following detailed description of illustrative embodiments of this invention described in connection with the drawings.

DESCRIPTION OF THE DRAWINGS

The illustrative embodiments may best be described by reference in the accompanying drawings where:

FIG. 5 is an exploded, perspective view of the movable knife of the knife assembly of FIG. 4.

Figure 1:
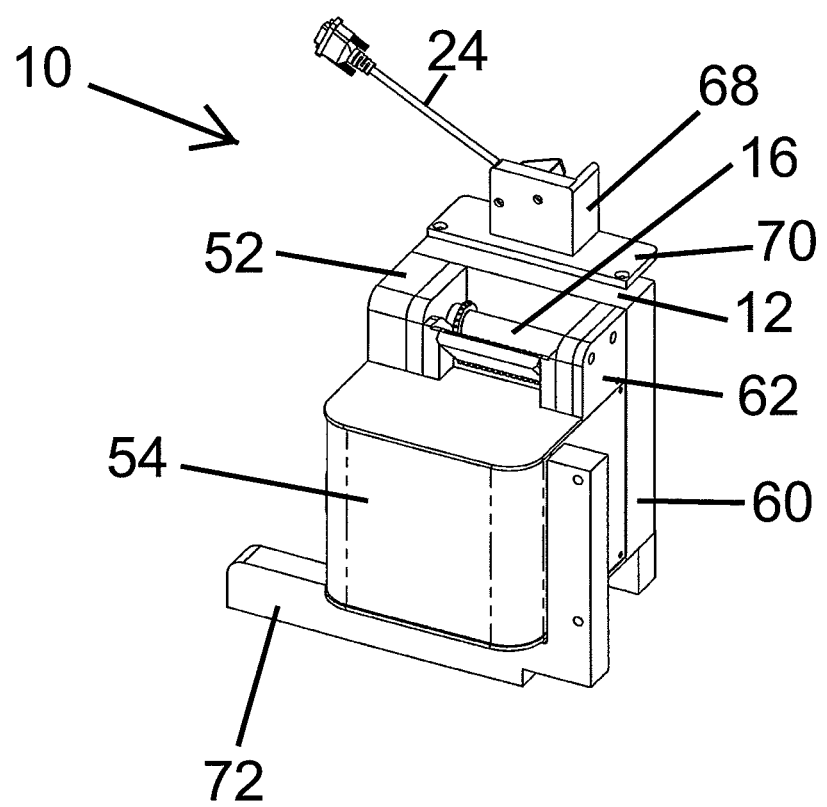
FIG. 1 is a perspective view of an apparatus for singulating micro-well tape according to the preferred teachings of the present invention.
Figure 2:
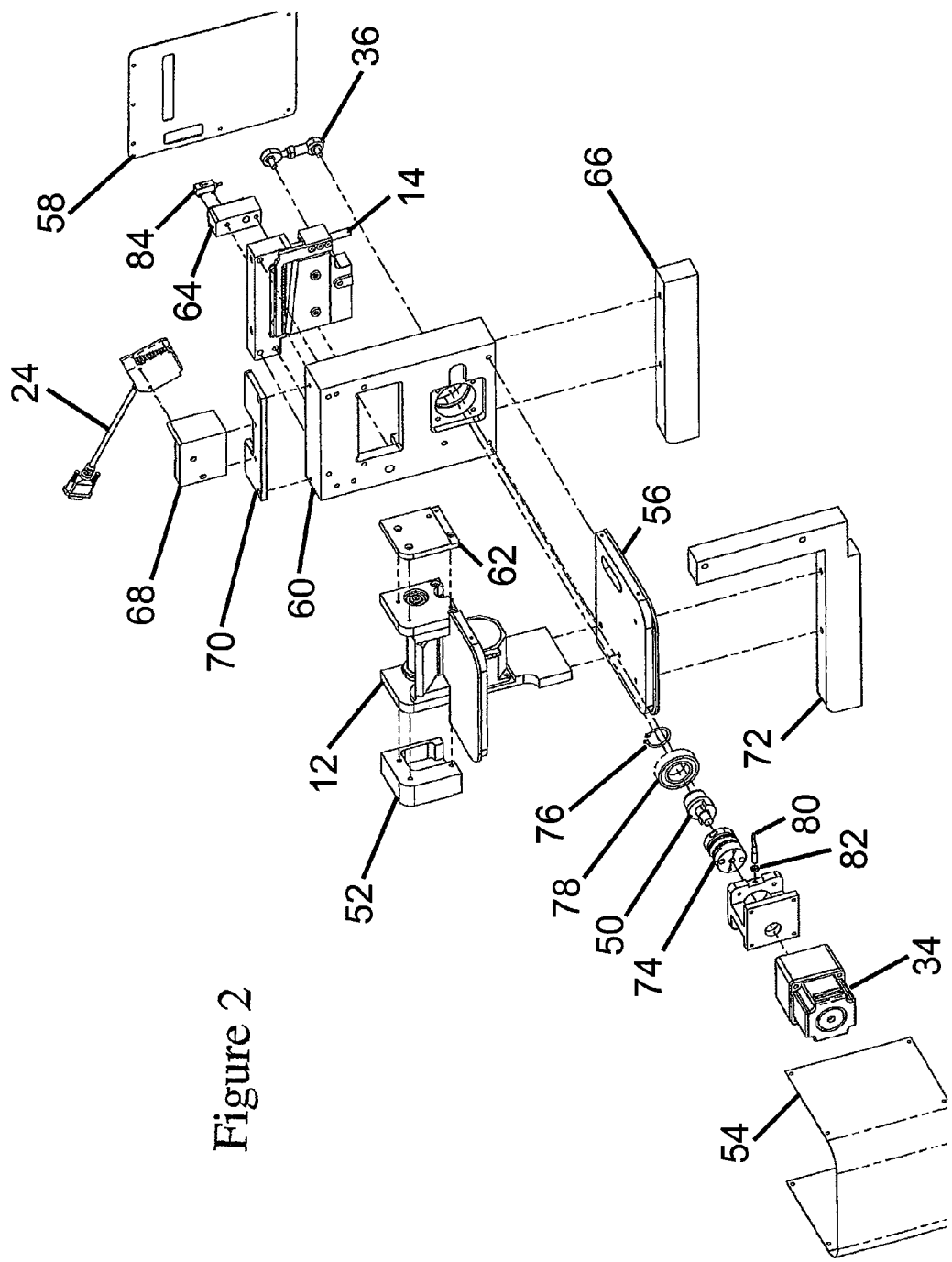
FIG. 2 is an exploded, perspective view of the apparatus of FIG. 1.
Figure 3:
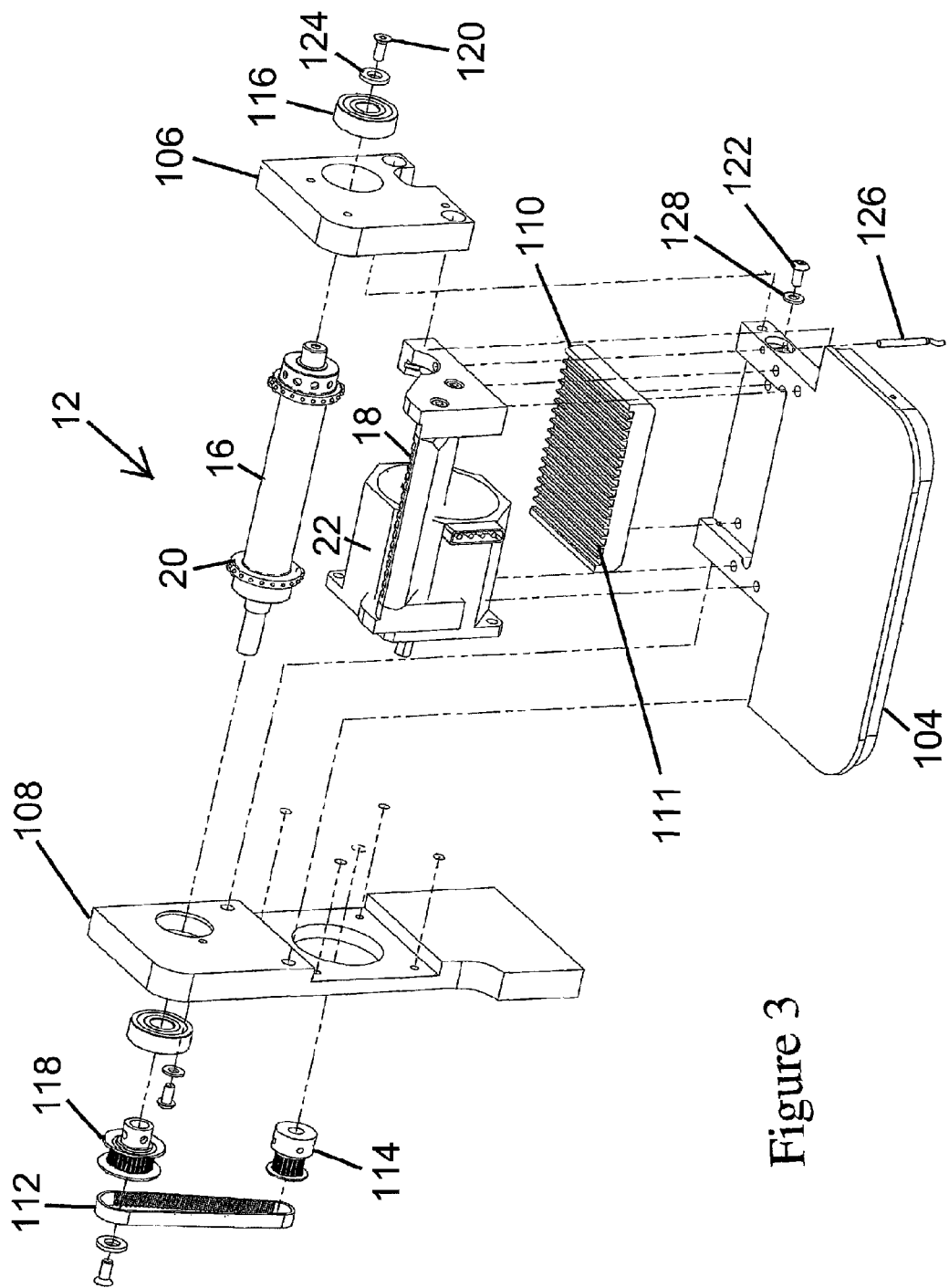
FIG. 3 is an exploded, perspective view of the tape drive of the apparatus of FIG. 1.
Figure 4:
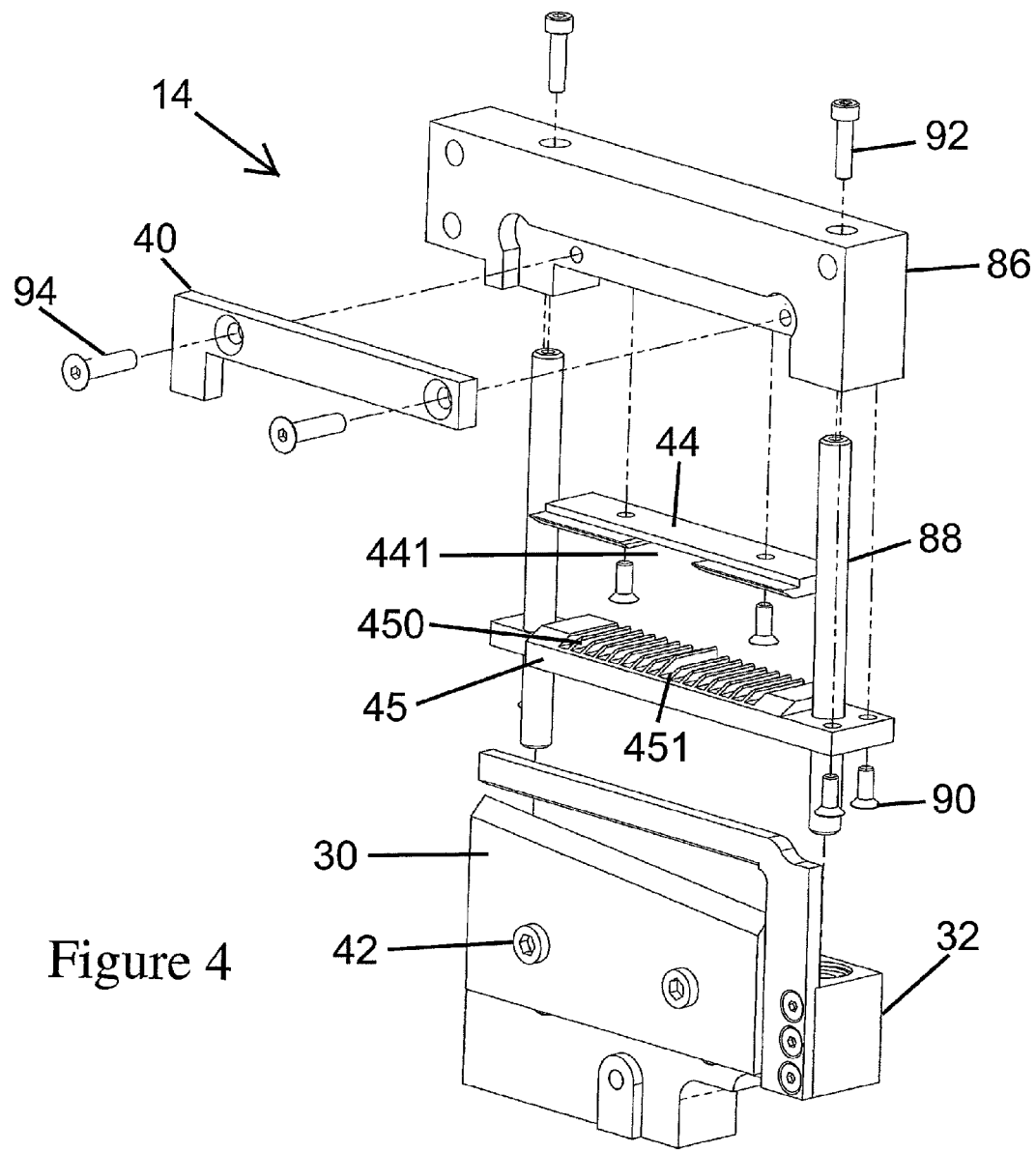
FIG. 4 is an exploded, perspective view of the knife assembly of the apparatus of FIG. 1.

All figures are drawn for ease of explanation of the basic teachings of the present invention only; the extensions of the figures with respect to number, position, relationship, and dimensions of the parts to form the preferred embodiments will be explained or will be within the skill of the art after the following description has been read and understood. Further, the exact dimensions and dimensional proportions to conform to specific force, weight, strength, and similar requirements will likewise be within the skill of the art after the following description has been read and understood.

Where used in the various figures of the drawings, the same numerals designate the same or similar parts. Furthermore, when the terms "top", "bottom", "first", "second", "forward", "rearward", "reverse", "front", "back", "height", "width", "length", "end", "side", "horizontal" "vertical", and similar terms are used herein, it should be understood that these terms have reference only to the structure shown in the drawings as it would appear to a person viewing the drawings and are utilized only to facilitate describing the illustrative embodiments.

DESCRIPTION OF THE PREFERRED EMBODIMENTS

An apparatus for singulating micro-well tape utilizing methods according to the preferred teachings of the present invention is shown in the drawings and generally designated 10. Particularly, apparatus 10 generally includes a tape drive 12 and a cutting assembly 14.

In the most preferred form shown, the tape drive 12 is of the tractor drive type. Specifically, a spool of empty or sealed, micro-well tape containing chemical compounds is placed on a spool holder. The free end of the tape is inserted between the tape drive shaft 16 and a backer plate 18 of the tape drive 12. Perforations on each edge and parallel to the plurality of rows of the array of wells of the tape mesh with pins 20 protruding from the drive shaft 16. A drive motor 22 turns the drive shaft 16 to advance the tape from between backer plate 18 and tape drive shaft 16 onto a tape guide 110 into the cutting assembly 14. Specifically, in the preferred form shown, tape drive shaft 16 is rotatably mounted between a bearing mount 106 and a drive mount 108 by bearings 116 received therein and retained therein by fasteners 120 sandwiching flat washers 124 against bearings 116. Drive motor 22 is suitably mounted to drive mount 108, with suitable provisions for rotatably interconnecting drive motor 22 and tape drive shaft such as a belt 112 extending around pulleys 114 and 118 fixed to the drive motor 22 and tape drive shaft 16 respectively as shown. In the preferred form, belt cover 52 is mounted to drive mount 108, and a side plate 62 is mounted to bearing mount 106 to prevent unintentional access to rotatable components of apparatus 10. Furthermore, in the preferred form shown, tape guide 110 is mounted in a stepped recess in a deck 104 which is secured to drive mount 108 and to which bearing mount 106, motor 22 and backer plate 18 are secured.

In the most preferred form, a proximity switch 126 is secured to deck 104 by fastener 122 passing through a washer 128 and passes through the side frame for backer plate 18. Furthermore, each of backer plate 18 and tape guide 110 includes a plurality of ridges 111 extending in a spaced, parallel relation to the movement direction of the micro-well tape. Specifically, ridges 111 are spaced to be slideably received between the rows of the array of wells in the micro-well tape and in the most preferred form with a single ridge 111 located between each adjacent pair of rows of the array of wells in the micro-well tape. It should be appreciated that the axis of tape drive shaft 16 extends perpendicular to the movement direction.

The film passes from the tape drive 12 through the cutting assembly 14 and into a tape holder. The tape drive motor 22 advances the tape until a barcode on the tape is detected by a sensor 24. The tape is then retracted to the cutting position. The tape is cut by the cutting assembly 14.

The cutting assembly 14 of the most preferred form shown includes a cutting knife blade 30 positioned below the tape and attached to a slide block 32. Specifically, slide block 32 is slideably mounted upon first and second slide shafts 88 extending from a cutter frame 86, with the slide shafts 88 secured to the cutter frame 86 by fasteners 92. In particular, slide shafts 88 are perpendicular to and the cutting knife blade 30 moves perpendicular to the movement direction of the micro-well tape.

The slide block 32 is moved vertically by a motor 34 and a connecting rod 36 in the preferred form shown. Particularly, servo class couplings 74 rotatably couple motor 34 to a drive crank/cam 50 rotatably mounted in a motor frame by a bearing 78 held in place by a snap ring 76. A proximity switch 80 held in place by nut 82 on the motor frame can be provided for detecting the rotational position of the drive crank/cam 50. Connecting rod 36 is connected between the drive crank/cam 50 and slide block 32. A photo-eye 84 is mounted by mount 64 to the singulation frame 60 for detecting the micro-well tape holder. In the preferred form shown, front guard panel 58 can be provided to extend over the singulation frame 60 to prevent unintentional access to connecting rod 36, shafts 88, blade 30, and other components. A guard 54 is secured to deck 104 and a bottom 56 secured to the lower end of drive mount 108 and to the singulation frame 60 to extend over motor 34 and associated components to prevent unintentional access. A base L bracket 72 is secured to bottom 56 and, with bracket 66, supports apparatus 10 in the form shown. Further, a sensor 24 is mounted by mount 68 extending from a light shield 70 mounted to the top of the singulation frame 60.

As the motor 34 turns, an eccentric motion produced by the drive crank/cam 50 moves the knife blade 30 up and down. An anvil 40 is positioned above the tape path. In the preferred form shown, anvil 40 is secured in a stepped recess in the cutter frame 86 by fasteners 94. In the preferred form shown, the knife blade 30 is retained on the slide block 32 by two bolts 42 and jam nuts 98 and can be tilted toward the anvil 40 to provide a positive shearing action. Specifically, in the preferred form, knife blade 30 is not flush with the slide block 32 but is allowed to tilt relative to slide block 32 on bolts 42. Ball plungers 100 are received in slide block 32 and abut knife blade 30 opposite of bolts 42 than the cutting edge. Ball plungers 100 push the knife blade 30 to tilt such that the cutting edge is against the anvil 40. The pushing by the ball plungers 100 limits the shearing clearance while also limiting the wear force, adjusting for blade wear, and acting as an overload if too much cutting force is encountered. The cutting edge 30 extends at an acute angle to the slide shafts 88 and generally perpendicular to the movement direction of the micro-well tape in the preferred form. A tape retriever 102 extending generally perpendicular to the slide shafts 88 and to the movement direction of the micro-well tape is further secured to slide block 32 by fasteners 96.

An upper tape retainer 44 is positioned above the tape path and in the most preferred form is secured to the cutter frame 86 such as by fasteners. The upper tape retainer 44 contacts the top face of the tape as the knife blade 30 and slide block 32 are moving upward and positions the cut end of the tape in a horizontal plane and at the same level as the film supply. In the preferred form, the upper tape retainer 44 includes a groove 441 extending in the movement direction and having a width perpendicular to the movement direction which is greater than a spacing between rows in the plurality of rows of the array of wells. A bottom tape retainer 45 is positioned below the tape path. This retainer 45 contacts the bottom face of the tape. In the preferred form shown, the bottom tape retainer 45 is secured to the cutter frame 86 such as by fasteners 90.

In the preferred form, the lower tape retainer 45 includes a multiplicity of ridges 450 corresponding to ridges 111 of backer plate 18 and tape guide 110. In particular, ridges 450 have a height from the bottom tape retainer 45 towards the top tape retainer 44 which is at least slightly greater than the height of the wells of the array of wells. In the preferred form shown, the center ridge of the plurality of ridges 450 is a raised ridge 451 having a height greater than the height of the remaining ridge 450. In the preferred form, raised ridge 451 extends into the groove 441 of the upper tape retainer 44.

Now that the basic construction of apparatus 10 according to the preferred teachings of the present invention has been set forth, a method of operation of apparatus 10 can be set forth and appreciated. Specifically, when the tape is cut by knife blade 30, at a cut interface including a trailing edge and a new leading edge, with the array of wells located between the initial leading edge and the trailing edge. The cut piece of tape is retained between the upper tape retainer 44 and the bottom tape retainer 45. Due to the raised ridge 451 of the bottom tape retainer 45 and the corresponding groove 441 in the upper tape retainer 44, the cut piece of tape is deflected into a corrugated shape. The height and width of the deflection is controlled by the height of the raised ridge 451 of the bottom tape retainer 45 and the width of the groove 441 of the upper tape retainer 44. It should be noted that as slide block 32 moves down after the cut, the tape retriever 102 moves below the anvil 40 and pushes the new leading edges of the tape into the normal path in the event that the new leading edge becomes propped against the anvil 40. Alternately, the tape can be withdrawn slightly opposite to the movement direction so that the new leading edge of the tape will not be propped up on the anvil 40.

It should be appreciated that lead edge of the incoming material is not deformed and remains generally flat, the material forming the micro-well tape being sufficiently rigid to hold a flat shape. The goal is to push the cut piece into another device without an additional feed mechanism. The difference in the shape at the cut-interface allows the new leading edge to push the trailing edge. As the cut interface enters the tape retainers 44 and 45, the new leading edge of the micro-well tape is guided into the tapered entry of the tape retainers 44 and 45. When the cut interface has passed beyond the tapered entry and fully between the tape retainers 44 and 45, then both the cut piece and the micro-well tape are deflected into the corrugated shape. The inner surfaces between the tape retainers 44 and 45 create a restricted space that is more than one material thickness but less than two material thicknesses. This restricted space maintains the new leading edge of the micro-well tape in a pushing relationship, preventing an overlap and the loss of pushing ability. It should be noted that the corrugated-pushing-geometry is designed to overlap with the restricted-space-pushing geometry. The overlap of pushing modes in the movement direction of travel is better than a gap between modes, or an immediate transition between modes. A gap between pushing modes would provide a region where pushing ability could be lost, causing overlap and jamming to occur. An immediate transition makes the loss of pushing ability less probable, however does not completely eliminate it.

The singulated, micro-well tape piece including the array of wells is now contained in the tape holder. The wells in the micro-well tape are aligned with a hole pattern in the upper surface of the tape holder. The reader is triggered to perform its usual tasks. The chemical results are analyzed and recorded.

After the well contents are analyzed, the tape holder is returned to its previous position by the reader. As the tape is advanced for the next cycle, this piece of micro-well tape that has been analyzed is pushed out of the tape holder.

The tape is then positioned in the correct position to be cut and the cycle is repeated.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

The invention claimed is:

1. Method for singulating comprising:
   advancing a micro-well tape including an array of wells including a plurality of rows, with the micro-well tape having a top face, a bottom face and a leading edge, with the micro-well tape being sufficiently rigid to hold a flat shape;
   inserting the leading edge between an upper tape retainer and a bottom tape retainer in a movement direction parallel to the plurality of rows of the array of wells, with the upper tape retainer positioned above the top face and with the bottom tape retainer positioned below the bottom face;
   passing the rows of the array of wells in the movement direction between a multiplicity of ridges on the bottom tape retainer after the leading edge is inserted, with the multiplicity of ridges having a height from the bottom tape retainer towards the upper tape retainer, with passing the rows including passing the micro-well tape over at least one of the multiplicity of ridges having a raised height greater than the height of remaining of the multiplicity of ridges to deflect the micro-well tape into a corrugated shape;
   cutting the micro-well tape perpendicular to the movement direction at a cut interface including a trailing edge and a new leading edge after the micro-well tape is passed over the at least one of the multiplicity of ridges, with the array of wells located intermediate the leading edge and the trailing edge; and
   inserting the new leading edge in the movement direction between the upper tape retainer and the lower retainer with the new leading edge pushing the trailing edge, with the micro-well tape being deflected by the at least one of the multiplicity of ridges, with the upper and lower tape retainers creating a restricted space to maintain a pushing relationship between the trailing edge and the new leading edge.

2. The method of claim 1 with passing the micro-well over the at least one of the multiplicity of ridges including extending the at least one of the multiplicity of ridges into a groove formed in the upper tape retainer, with the groove having a width perpendicular to the movement direction greater than a spacing between rows in the plurality of rows of the array of wells.

3. The method of claim 2 with inserting the leading edge comprising inserting the leading edge between tapered entries of the upper and bottom tape retainers, with the tapered entries having decreasing height in the movement direction.

4. The method of claim 3 with cutting the micro-well tape comprising moving a cutting knife blade from below the micro-well tape to engage an anvil positioned above the micro-well tape, with the anvil and the upper tape retainer mounted to a cutter frame generally perpendicular to each other.

5. The method of claim 4 with moving the cutting knife blade comprising sliding a slide block perpendicular to the movement direction on slide shafts and mounting the cutting knife blade thereon, with the slide shafts extending from the cutter frame.

6. The method of claim 5 with advancing the micro-well tape comprising meshing pins protruding from a rotating tape drive shaft extending perpendicularly to the movement direction and through perforations along the edges of the micro-well tape and parallel to the plurality of rows of the array of wells.

7. The method of claim 6 with advancing the micro-well tape comprising inserting the micro-well tape between the tape drive shaft and a backer plate including a multiplicity of ridges corresponding to the multiplicity of ridges on the bottom tape retainer.

8. The method of claim 7 with passing the micro-well tape including detecting a bar code on the micro-well tape by a sensor with cutting the micro-well tape occurring after detection of the bar code.

9. The method of claim 1 with inserting the leading edge comprising inserting the leading edge between tapered entries of the upper and bottom tape retainers, with the tapered entries having decreasing height in the movement direction.

10. The method of claim 1 with cutting the micro-well tape comprising moving a cutting knife blade from below the micro-well tape to engage an anvil positioned above the micro-well tape, with the anvil and the upper tape retainer mounted to a cutter frame generally perpendicular to each other.

11. The method of claim 1 with advancing the micro-well tape comprising meshing pins protruding from a rotating tape drive shaft extending perpendicularly to the movement direction and through perforations along the edges of the micro-well tape and parallel to the plurality of rows of the array of wells.

12. The method of claim 1 with passing the micro-well tape including detecting a bar code on the micro-well tape by a sensor with cutting the micro-well tape occurring after detection of the bar code.

* * * * *